(12) United States Patent
Jiang et al.

(10) Patent No.: US 12,369,886 B2
(45) Date of Patent: Jul. 29, 2025

(54) ULTRASOUND PROBE HAVING THREE CONFIGURABLE BUTTONS

(71) Applicant: BFLY OPERATIONS, INC., Burlington, MA (US)

(72) Inventors: Emily Jiang, Brooklyn, NY (US); Dora Fang, Baltimore, MD (US); Teresa Lopez, Plainville, CT (US); Josephine Lau, Brooklyn, NY (US); Murad Omar, Secaucus, NJ (US)

(73) Assignee: BFLY OPERATIONS, INC., Burlington, MA (US)

( * ) Notice: Subject to any disclaimer, the term of this patent is extended or adjusted under 35 U.S.C. 154(b) by 16 days.

(21) Appl. No.: 18/421,061

(22) Filed: Jan. 24, 2024

(65) Prior Publication Data

US 2024/0277316 A1 Aug. 22, 2024

Related U.S. Application Data

(60) Provisional application No. 63/446,088, filed on Feb. 16, 2023.

(51) Int. Cl.
*A61B 8/00* (2006.01)

(52) U.S. Cl.
CPC .......... *A61B 8/4455* (2013.01); *A61B 8/4427* (2013.01); *A61B 8/465* (2013.01); *A61B 8/467* (2013.01); *A61B 8/5246* (2013.01); *A61B 8/54* (2013.01)

(58) Field of Classification Search
CPC .................................. A61B 8/54; A61B 8/467
See application file for complete search history.

(56) References Cited

U.S. PATENT DOCUMENTS

| | | | |
|---|---|---|---|
| 8,695,429 B2 | 4/2014 | Urbano et al. | |
| 9,402,601 B1 | 8/2016 | Berger et al. | |
| 9,667,889 B2 | 5/2017 | Rothberg | |
| 10,799,913 B2 | 10/2020 | Bales, Jr. et al. | |
| 11,179,175 B2 | 11/2021 | Houser et al. | |
| 2002/0177774 A1* | 11/2002 | Hwang | G01S 15/892 600/441 |
| 2006/0176242 A1 | 8/2006 | Jaramaz et al. | |
| 2007/0093713 A1* | 4/2007 | Byron | A61B 8/461 600/437 |

(Continued)

*Primary Examiner* — Colin T. Sakamoto
(74) *Attorney, Agent, or Firm* — Carter, DeLuca & Farrell LLP; Vadim Vapnyar (57) ABSTRACT

An ultrasound system includes an ultrasound probe and a mobile device in operative communication with each other. The ultrasound probe includes three buttons—an up button, a center button, and a down button—disposed on the external housing. The mobile device may be configured to receive an indication from the ultrasound probe of a double press of the center button when the mobile device is displaying a scan screen. Based on the double press of the center button, the mobile device may be configured to display a button function configuration menu on the scan screen, receive a selection from the button function configuration menu of a button function configuration, receive an indication of a single press of the up button or the down button, and perform an action in accordance with the single press of the up button or the down button and the button function configuration.

20 Claims, 7 Drawing Sheets

(56) References Cited

U.S. PATENT DOCUMENTS

| | | |
|---|---|---|
| 2011/0055447 A1 | 3/2011 | Costa |
| 2012/0197131 A1* | 8/2012 | Georgiev ............. A61B 8/4455 |
| | | 600/459 |
| 2014/0276069 A1* | 9/2014 | Amble ................. A61B 8/4488 |
| | | 600/447 |
| 2015/0190114 A1* | 7/2015 | Ninomiya .............. A61B 8/467 |
| | | 600/437 |
| 2017/0105701 A1 | 4/2017 | Pelissier et al. |
| 2017/0360397 A1 | 12/2017 | Rothberg et al. |
| 2018/0055483 A1* | 3/2018 | Hunter ................... A61B 8/467 |
| 2019/0038260 A1* | 2/2019 | Lee ........................ A61B 8/582 |
| 2019/0175149 A1 | 6/2019 | Dickie et al. |
| 2020/0129155 A1 | 4/2020 | Elgena et al. |
| 2020/0214679 A1 | 7/2020 | Silberman et al. |
| 2021/0096243 A1 | 4/2021 | Gafner et al. |
| 2021/0244386 A1 | 8/2021 | Bellamkonda et al. |
| 2021/0330296 A1 | 10/2021 | Silberman et al. |
| 2021/0401404 A1* | 12/2021 | Hageman ............. A61B 8/5207 |
| 2022/0304660 A1* | 9/2022 | Loype ...................... A61B 8/54 |

\* cited by examiner

ULTRASOUND PROBE HAVING THREE CONFIGURABLE BUTTONS

CROSS-REFERENCE TO RELATED APPLICATIONS

This application claims the benefit of, and priority to, U.S. Provisional Patent Application Ser. No. 63/446,088 filed on Feb. 16, 2023. The entire contents of the foregoing application is incorporated by reference herein.

FIELD

Generally, the aspects of the technology described herein relate to ultrasound devices. Certain aspects relate to an ultrasound probe having three programmable buttons.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time the wave takes to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the present technology, an ultrasound system includes an ultrasound probe and a mobile device in operative communication with the ultrasound device and running an ultrasound application. The ultrasound probe includes a transducer head, an external housing, and three buttons disposed on the external housing vertically along a direction of a longitudinal axis of the ultrasound probe. The three buttons include an up button closest to the transducer head, a down button farthest from the transducer head, and a center button between the up button and the down button. The mobile device is configured to: receive an indication from the ultrasound probe of a double press of the center button when the mobile device is displaying a scan screen, where ultrasound data captured by the ultrasound probe and transmitted to the mobile device is displayed on the scan screen as ultrasound images that are updated in real-time; based on the receiving the indication of the double press of the center button, display a button function configuration menu on the scan screen; receive a selection from the button function configuration menu of a button function configuration; receive an indication of a single press of the up button or the down button; and perform an action in accordance with the single press of the up button or the down button and the button function configuration.

In some embodiment, the button function configuration menu includes multiple selectable options for functions of the up button and the down button, and the multiple selectable options include adjust depth, adjust gain, and change mode. In some embodiments, the button function configuration menu includes a list of options and a selection indicator that highlights an option in the list, and the mobile device is configured, when receiving the selection from the button function configuration menu of the button function configuration, to: receive an indication from the ultrasound probe of a press of the up button or the down button and move the location of the selection indicator in the list up or down, respectively; and receive an indication from the ultrasound probe of a press of the center button and set the option in the list highlighted by the selection indicator as the button function configuration. In some embodiments, the button function configuration menu includes a list of options, and the mobile device is configured, when receiving the selection from the button function configuration menu of the button function configuration, to detect a touch from a user of one of the options on a touch-sensitive display screen of the mobile device. In some embodiments, the mobile device is configured to overlay the button function configuration menu on the scan screen.

In some embodiments, the selected button function configuration is adjusting imaging depth, and the mobile device is configured, when performing the action, to receive an indication from the ultrasound probe of a press of the up button or the down button and cause the imaging depth to increase or decrease, respectively. In some embodiments, the mobile device is configured to cause the imaging depth to increase or decrease by 1 cm for a single button press. In some embodiments, the mobile device is configured, when causing the imaging depth to increase or decrease, to transmit one or more commands to the ultrasound probe to change one or more aspects of how the ultrasound waves transmits ultrasound waves. In some embodiments, the one or more aspects are selected from the group consisting of pulse repetition rate, focal depth, frequency, pulse length, and aperture size.

In some embodiments, the selected button function configuration is adjusting gain, and the mobile device is configured, when performing the action, to receive an indication from the ultrasound probe of a press of the up button or the down button and cause the imaging gain to increase or decrease, respectively. In some embodiments, the mobile device is configured to cause the imaging gain to increase or decrease by 5% for a single button press.

In some embodiments, the selected button function configuration is adjusting mode, and the mobile device is configured, when performing the action, to receive an indication from the ultrasound probe of a press of the up button or the down button and to cycle through a list of ultrasound imaging modes including two or more of B-mode, color Doppler, power Doppler, M-mode, and pulsed Doppler. In some embodiments, the mobile device is configured, when cycling through the list of ultrasound imaging modes, to transmit one or more commands to the ultrasound probe to change one or more aspects of how the ultrasound probe transmits ultrasound waves and/or one or more aspects of how the ultrasound probe receives ultrasound waves.

In some embodiments, a user is logged into an account on the ultrasound application, and the button function configuration persists until the user logs out of the account on the ultrasound application. In some embodiments, the mobile device is configured to save the button function configuration locally.

In some embodiments, the selected button function configuration is adjusting imaging depth, and the mobile device is configured, when performing the action, to receive an indication from the ultrasound probe of a long press of the up button or the down button and cause the imaging depth to continuously increase or decrease, respectively. In some embodiments, the selected button function configuration is adjusting gain, and the mobile device is configured, when performing the action, to receive an indication from the ultrasound probe of a long press of the up button or the down button and cause the imaging gain to continuously increase or decrease, respectively. In some embodiments, the mobile device is configured to receive an indication from the ultrasound probe of a long press of the center button and perform an action selected from the group consisting of: capturing a cine of ultrasound images; disabling the up button, the down button, and the center button; display the button function configuration menu; and toggle on or off one or more artificial intelligence features.

According to one aspect of the present technology, an ultrasound system includes an ultrasound probe and a mobile device in operative communication with the ultrasound probe and running an ultrasound application. The ultrasound probe includes a transducer head, an external housing, and three buttons disposed on the external housing vertically along a direction of a longitudinal axis of the ultrasound probe. The three buttons include an up button closest to the transducer head, a down button farthest from the transducer head, and a center button between the up button and the down button. The mobile device is configured to receive a selection from a preferences screen of a button function configuration from among a plurality of button function configuration options including: pressing the center button causes capture of an ultrasound image, pressing the up button causes increase in imaging depth, and pressing the down button causes decrease in imaging depth; pressing the center button causes capture of a cine of ultrasound images to start or stop, pressing the up button causes increase in imaging depth, and pressing the down button causes decrease in imaging depth; pressing the center button causes capture of an ultrasound image, pressing the up button causes increase in imaging gain, and pressing the down button causes decrease in imaging gain; and pressing the center button causes capture of a cine of ultrasound images to start or stop, pressing the up button causes increase in imaging gain, and pressing the down button causes decrease in imaging gain; receive an indication of a single press of the up button, the down button, or the center button; and perform an action in accordance with the single press of the up button, the down button, or the center button, and the selected button function configuration.

In some embodiments, the plurality of button function configuration options further include: pressing the center button causes capture of an ultrasound image and pressing the up and down buttons causes change of mode; and pressing the center button causes capture of a cine of ultrasound images to start or stop and pressing the up and down buttons causes change of mode.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Recently, point-of-care ultrasound system have been developed. Such a system may include an ultrasound probe in operative communication with a mobile device, such as a smartphone or tablet, and may be cheaper and more portable than a conventional cart-based ultrasound system. The mobile device may run an ultrasound application ("app") that enables a user to configure the ultrasound probe for a particular type of ultrasound scan, modify various ultrasound imaging settings (e.g., mode, depth, and gain), receive ultrasound data from the ultrasound probe, display ultrasound images, and upload ultrasound images to the cloud. Modifying ultrasound imaging settings is typically performed by a user making selections on the touch-sensitive display screen of the mobile device. However, this may be difficult when the user is simultaneously holding the ultrasound probe and the mobile device, when the mobile device is mounted somewhere out of reach of the user, or when the user is wearing gloves. As an example of the latter, a user may not want to touch several surfaces when performing interventional procedures such as a biopsy, fine needle aspiration, or for peripheral vascular access. For those procedures, a user may wear sterile gloves and place a cover over the ultrasound probe. Touching the mobile screen, or any other surface, increases the probability of infection transfer.

The inventors have developed technology including an ultrasound probe having a set of three programmable buttons disposed on the external housing of the probe. These buttons may enable a user to modify ultrasound imaging settings from the probe itself, rather than the mobile device. The programmability may enable users to configure the buttons according to their own preferences, and to configure the buttons during scanning. In the case of an interventional procedure, probe buttons may allow the user to modify ultrasound imaging settings by touching a smaller, sterile surface area on the ultrasound probe rather than touching the mobile device.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Figure 1:
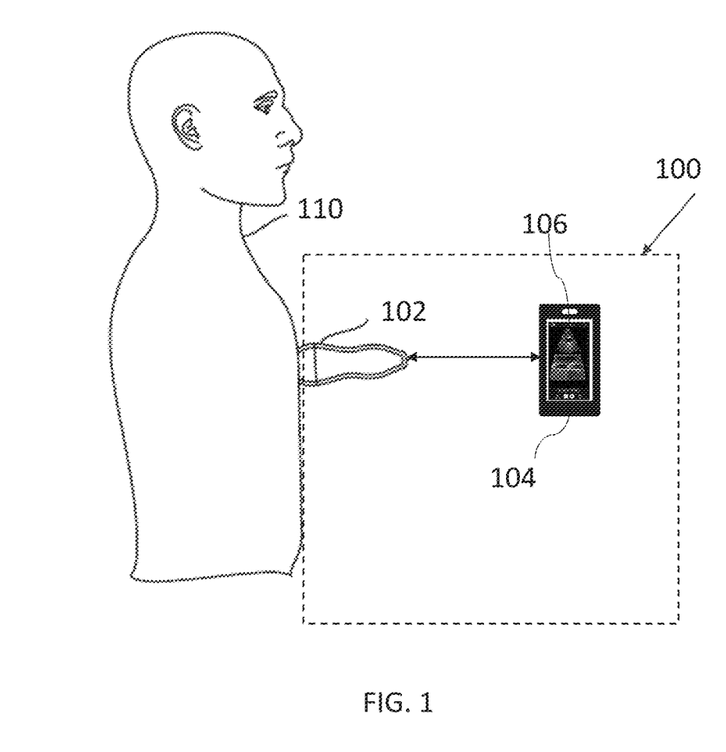
FIG. 1 illustrates an example of an ultrasound system including an ultrasound probe, in accordance with certain embodiments described herein.

FIG. 1 illustrates an exemplary ultrasound system 100, in accordance with certain embodiments described herein. The ultrasound system 100 includes an ultrasound probe 102 and a mobile device 104 (e.g., a smartphone or tablet) running an ultrasound application ("app") 106. The ultrasound probe 102 is used to scan a patient 110. The mobile device 104 is in operative communication with the ultrasound probe 102 over a wired connection (e.g., a USB or Lightning cable) or a wireless connection (e.g., over a Wi-Fi or Bluetooth connection). (It should be appreciated that in some embodiments the mobile device 104 and the ultrasound probe 102 may be in operative communication only over a wired connection, in some embodiments the mobile device 104 and the ultrasound probe 102 may be in operative communication only over a wireless connection, and in some embodiments the mobile device 104 and the ultrasound probe 102 may be in operative communication over either or both of a wired connection and a wireless connection.) The ultrasound application 106 enables a user to interface with the ultrasound probe 102. For example, the ultrasound application 106 may enable a user to use graphical user interfaces (GUIs) displayed on the mobile device 104 to configure the ultrasound probe 102 for a particular type of ultrasound scan, modify various ultrasound imaging settings (e.g., mode, depth, and gain), receive ultrasound data from the ultrasound probe 102, display ultrasound images in the GUI, and upload ultrasound images to the cloud (i.e., one or more servers and software and databases on those servers) which the mobile device 104 can access.

Figure 2:
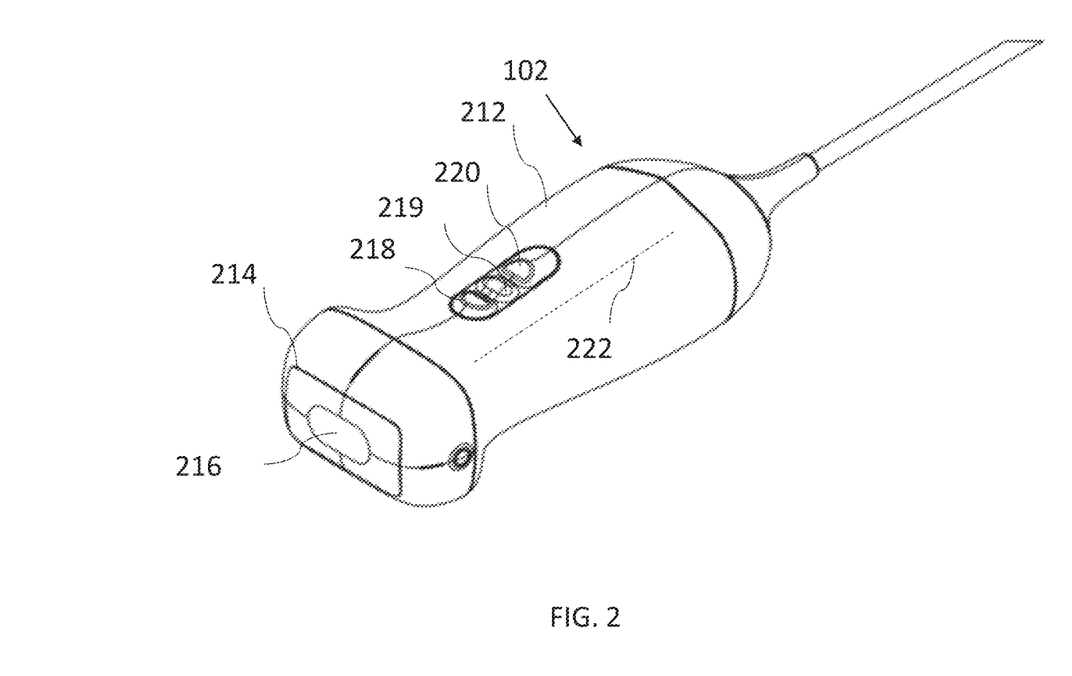
FIG. 2 illustrates in more detail the ultrasound probe of FIG. 1, in accordance with certain embodiments described herein.

FIG. 2 illustrates in more detail the ultrasound probe 102, in accordance with certain embodiments described herein. The ultrasound probe 102 has an external housing 212, a transducer head 214, and three buttons 218-220 disposed on the external housing 212. The transducer head 214 includes an array of ultrasonic transducers 216 configured to transmit and receive ultrasonic waves. The three buttons 218-220 may be arranged vertically along the direction of the longitudinal axis 222 of the ultrasound probe 102. The three buttons may be referred to as the up button 218, the center button 219, and the down button 220, where the up button 218 is closest to the transducer head 214, the down button 220 is farthest from the transducer head 214, and the center button 219 is between the up button 218 and the down button 220.

Figure 3:
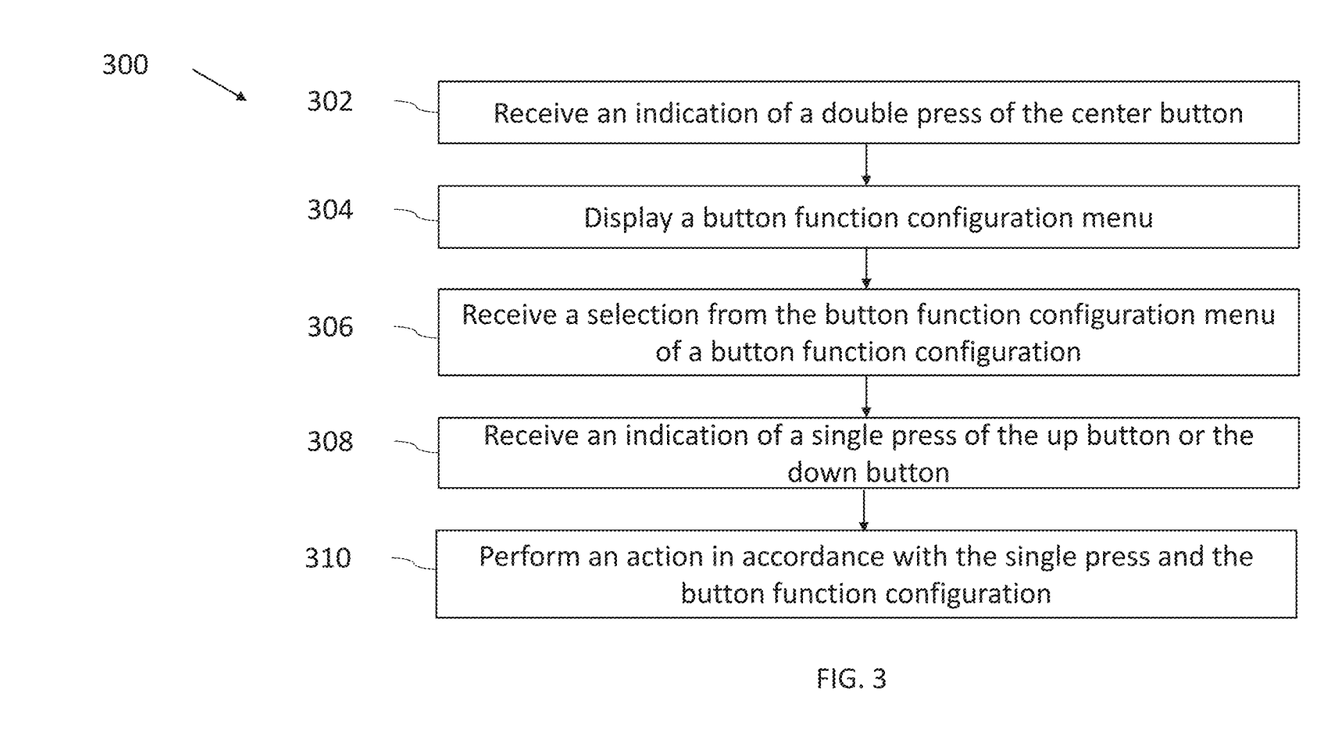
FIG. 3 illustrates a process for configuration of the three buttons on the ultrasound probe, in accordance with certain embodiments described herein.

The three buttons 218-220 may be configurable by a user. The user may use the mobile device 104 to configure the three buttons 218-220. FIG. 3 illustrates an exemplary process 300 for configuration of the three buttons 218-220 on the ultrasound probe 102, in accordance with certain embodiments described herein. The process 300 may be performed by the mobile device 104.

Figure 4:
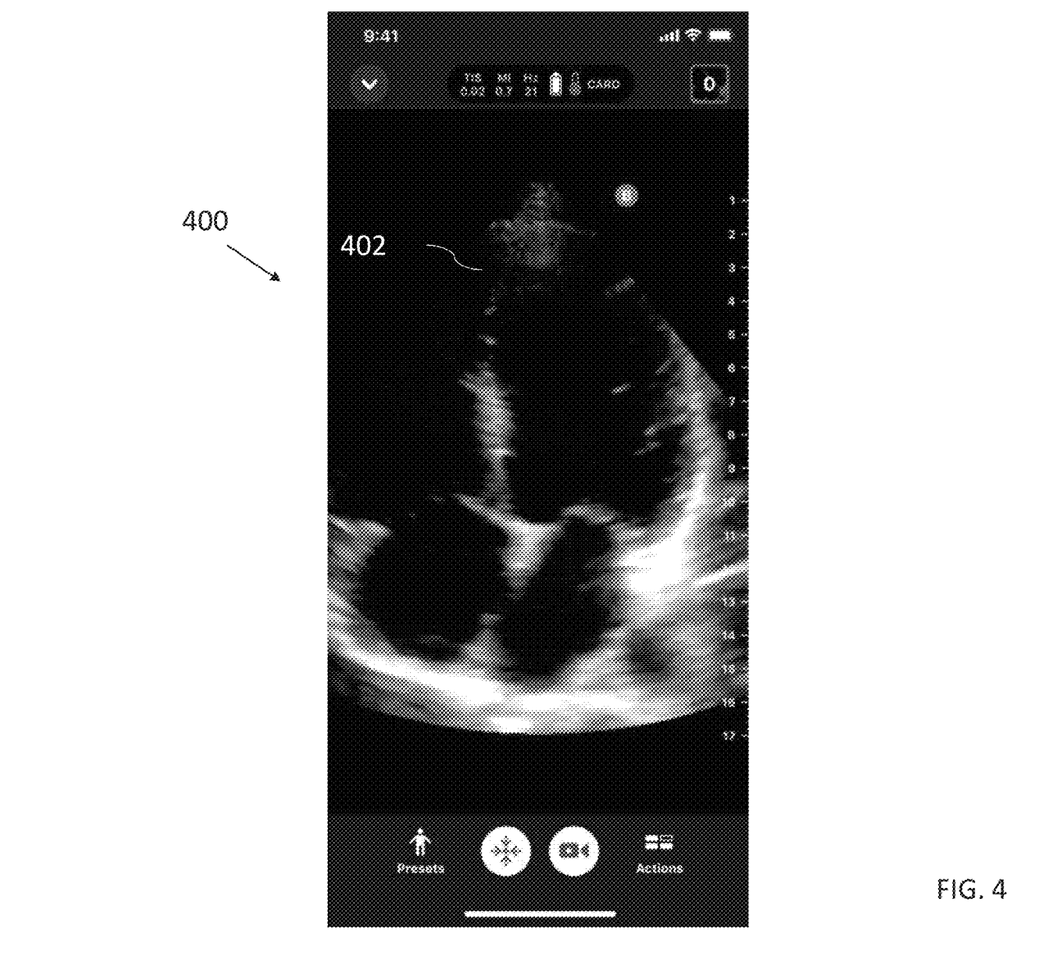
FIG. 4 illustrates an example of a scan screen, in accordance with certain embodiments described herein.

At step 302, the mobile device 104 receives an indication from the ultrasound probe 102 of a double press of the center button 219. For example, the ultrasound probe 102 may detect the double press of the center button 219 and transmit an indication of this double press of the center button 219 to the mobile device 104 over the wired or wireless connection between the ultrasound probe 102 and the mobile device 104. In some embodiments, the double press of the center button 219 may be performed by the user when the mobile device 104 is displaying a scan screen, in which ultrasound data being captured by the ultrasound probe 102 and transmitted to the mobile device 104 is displayed on the mobile device 104 as ultrasound images that are updated in real-time. In other words, the button configuration menu may be displayed during scanning, when the ultrasound probe 102 is collecting ultrasound data. FIG. 4 illustrates an exemplary scan screen 400, in accordance with certain embodiments described herein. The scan screen 400 displays ultrasound images 402 that are updated in real-time.

Figure 5:
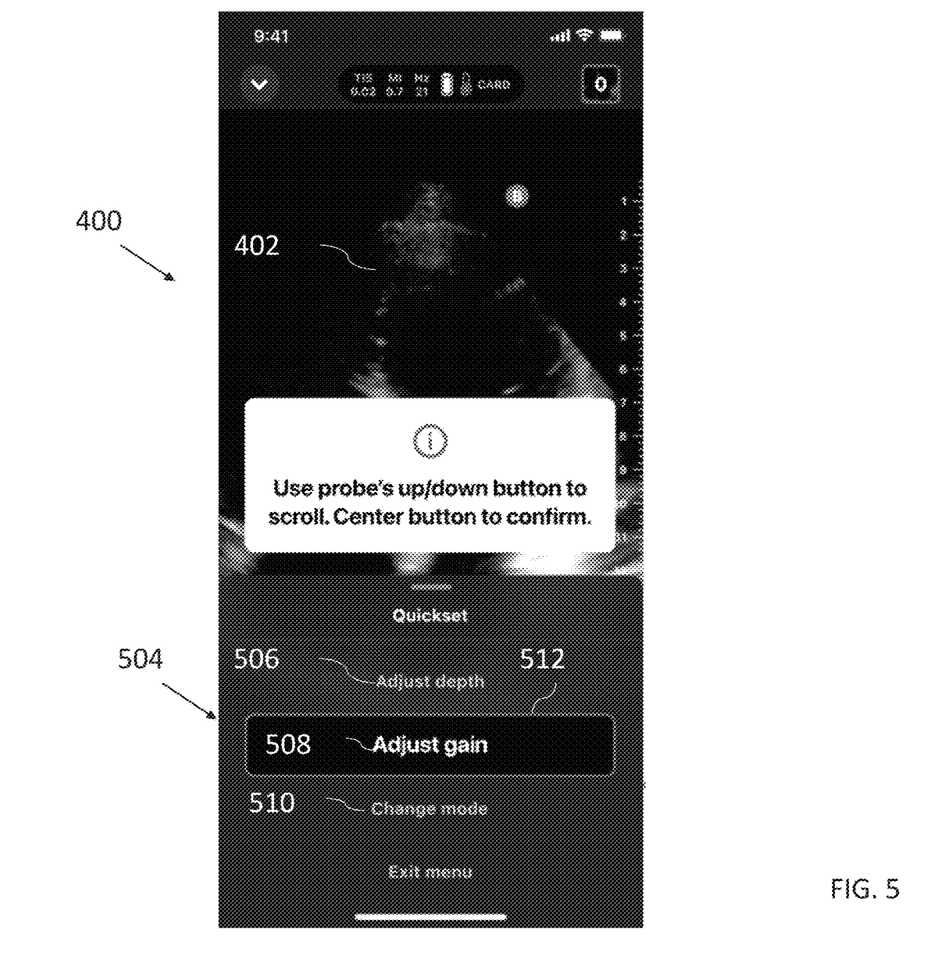
FIG. 5 illustrates another example of the scan screen, in accordance with certain embodiments described herein.

At step 304, based on receiving the indication from the ultrasound probe 1A02 of the double press of the center button 219, the mobile device 104 displays a button function configuration menu. The configuration menu may present multiple selectable options for the functions of the up button 218 and the down button 220. For example, the selectable options may be adjust depth, adjust gain, and change mode. In some embodiments, the button function configuration menu may be displayed on the scan screen. FIG. 5 illustrates another example of the scan screen 400, in accordance with certain embodiments described herein. FIG. 5 illustrates a button function configuration menu 504 which may be displayed after a double press of the center button 219. The button function configuration menu 504 is shown on the screen. In some embodiments, such as the example of FIG. 5, the mobile device 104 overlays the button function configuration menu 504 on the scan screen 400. In such embodiments, some or most of the rest of the scan screen 400 may still be visible. Thus, the user may be able to configure the buttons without having to leave the scan screen 400. The button function configuration menu 504 includes a list of options, namely an adjust depth option 506, an adjust gain option 508, and a change mode option 510. A selection indicator 512 highlights one of the options in the list.

In some embodiments, instead of the mobile device 104 displaying the button function configuration menu (at step 304) in response to an indication of a double press of the center button 219 (received at step 302), the mobile device 104 may display the button configuration in response to an indication of a single press of the center button 219, or a long press (i.e., longer than a threshold period of time) of the center button 219. In some embodiments, if the user has not yet selected a button function configuration, and the user presses any of the buttons 218-220, the mobile device 104 may display the button function configuration menu. Alternatively, if the user has not yet selected a button function configuration, and the user presses the up button 218 or the down button 220, no action may occur.

At step 306, the mobile device 104 receives a selection from the button function configuration menu of a button function configuration. For example, if the selectable options are adjust depth, adjust gain, and change mode, the mobile device 104 may receive a selection of either adjust depth, adjust gain, or change mode. In some embodiments, the options in the button function configuration may be displayed as a list, and the user may use the buttons 218-220 to scroll through the options in the list. Pressing the up button 218 may move a selection indicator (e.g., the selection indicator 512) up in the list of options, pressing the down button 220 may move the selection indicator down in the list of options, and pressing the center button 219 may cause selection of the option currently highlighted by the selection indicator. In such embodiments, the mobile device 104 may receive an indication from the ultrasound probe 102 of a press of the up button 218 or the down button, and move the location of the selection indicator in the list up or down, respectively. If the selection indicator is at the top of the list and the up button 218 is pressed, the selection indicator may move to the bottom of the list. If the selection indicator is at the bottom of the list and the down button 220 is pressed, the selection indicator may move to the top of the list. The mobile device 104 may receive an indication from the ultrasound probe 102 of a press of the center button 219 and set the option in the list highlighted by the selection indicator as the button function configuration. In the example of FIG. 5, pressing the center button 219 while the selection indicator 512 is on the adjust gain option 508 would cause selection of the adjust gain configuration. In some embodiments, the user may touch the screen of the mobile device 104 to select one of the options. In such embodiments, the mobile device 104 may detect a touch from a user of one of the options on a touch-sensitive display screen of the mobile device 104. In some embodiments, the user may use either method (i.e., pressing the buttons 218-220 in the ultrasound probe 102 or touching the display screen of the mobile device 104). Once the selection has been made, the button function configuration menu may disappear from the scan screen.

At step 308, the mobile device 104 receives an indication of a single press of the up button 218 or down button 220. For example, the ultrasound probe 102 may detect the single press of the up button 218 or down button 220 and transmit an indication of this single press over the wired or wireless connection between the ultrasound probe 102 and the mobile device 104.

At step 310, the mobile device 104 performs an action in accordance with the single press of a button (from step 308) and the button function configuration (from step 306). For example, consider that the button function configuration option of adjust depth was received at step 306. The mobile device 104 may receive an indication from the ultrasound probe 102 of a press of the up button 218 or the down button 220 and cause the imaging depth to increase or decrease, respectively. Imaging depth may refer to the maximum depth within the patient 110 to which the ultrasound images displayed by the scan screen descends. The increase or decrease in imaging depth may be by a predetermined amount in response to each single press. For example, the mobile device 104 may cause the imaging depth to increase or decrease by 1 cm for a single press of the up button 218 or the down button 220. To cause the imaging depth to increase or decrease, the mobile device 104 may transmit one or more commands to the ultrasound probe 102 over the wired or wireless connection. For example, the mobile device 104 may transmit one or more commands to the ultrasound probe 102 to change one or more aspects of how the ultrasound probe 102 transmits ultrasound waves. Such aspects may include pulse repetition rate, focal depth, frequency, pulse length, and/or aperture size, as non-limiting examples.

As another example, consider that the button function configuration option of adjust gain was received at step 306. The mobile device 104 may be configured, when performing the action, to receive an indication from the ultrasound probe 102 of a press of the up button 218 or the down button 220 and cause the imaging gain to increase or decrease, respectively. Imaging gain may refer to uniform increase or decrease of the brightness of pixels in the ultrasound images displayed on the scan screen. The increase or decrease in imaging gain may be by a predetermined amount in response to each single press. For example, the mobile device 104 may cause the imaging gain to increase or decrease by 5% for a single press of the up button 218 or the down button 220.

As another example, consider that the button function configuration option of change mode was received at step 306. The mobile device 104 may receive an indication from the ultrasound probe 102 of a press of the up button 218 or the down button 220 and cycle through a list of ultrasound imaging modes. The list of ultrasound imaging modes may include two or more of B-mode, color Doppler, power Doppler, M-mode, and pulsed Doppler. In response to a press of the up button 218, the mobile device 104 may cause the imaging mode to change to the next mode in a particular sequence of modes. In response to a press of the down button 220, the mobile device 104 may cause the imaging mode to change to the previous mode in a particular sequence of modes. An example of a sequence of modes may be, for example, B-mode, color Doppler, power Doppler, M-mode, and pulsed Doppler. Thus, if the current mode is B-mode and the up button 218 is pressed, the mode may change to color Doppler. If the up button 218 is pressed again, the mode may change to power Doppler. If the down button 220 is pressed, the mode may change to color Doppler. If the up button 218 is pressed when the mode is at the last mode in the sequence, the mode may revert to the first mode in the sequence. If the down button 220 is pressed when the mode is at the first mode in the sequence, the mode may revert to the last mode in the sequence. To cause the mode to change, the mobile device 104 may transmit one or more commands to the ultrasound probe 102 over the wired or wireless connection. For example, the mobile device 104 may transmit one or more commands to the ultrasound probe 102 to change one or more aspects of how the ultrasound probe 102 transmits ultrasound waves and/or one or more aspects of how the ultrasound probe 102 receives ultrasound waves.

In some embodiments, the mobile device 104 may also receive an indication of a long press (i.e., lasting longer than a threshold period of time) of the up button 218 or down button 220, and perform an action based on the long press and the selected button function configuration. For example, if the selected button function configuration is adjust depth, then the mobile device 104 may receive an indication from the ultrasound probe 102 of a long press of the up button 218 or the down button 220 and cause the imaging depth to continuously increase or decrease, respectively. A continuous change in the imaging depth may be a change that occurs at a certain rate (e.g., 1 cm per second) as long as the button is held down. As another example, if the selected button function configuration is change gain, then the mobile device 104 may receive an indication from the ultrasound probe 102 of a long press of the up button 218 or the down button 220 and cause the imaging gain to continuously increase or decrease, respectively. For example, the imaging gain may change at a certain rate (e.g., 5% per second) as long as the button is held down. An action in response to a long button press may occur after the button has been pressed for the threshold period of time and last until the button is released.

In some embodiments, when the mobile device 104 receives an indication from the ultrasound probe 102 of a single press of the center button 219, the mobile device 104 may capture the current ultrasound image displayed on the scan screen. In some embodiments, when the mobile device 104 receives an indication from the ultrasound probe 102 of a single press of the center button 219, the mobile device 104 may begin to capture a cine of ultrasound images beginning with the current ultrasound image displayed on the scan screen, and when the mobile device 104 receives another indication from the ultrasound probe 102 of a single press of the center button 219, the mobile device 104 may stop capture of the cine. In some embodiments, a user may configure the mobile device 104 (e.g., through a configuration screen displayed on the mobile device 104) as to which of the two options (i.e., whether to capture an image or a cine) to perform based on a single press of the center button 219.

In some embodiments, the ultrasound system 100 may enter a low-power mode after a period of inactivity (e.g., after the user has not interacted with the ultrasound probe 102 and/or the mobile device 104 for a threshold period of time) to conserve the battery power and reduce the temperature of the ultrasound probe 102. When the ultrasound system 100 enters the low-power mode, the ultrasound system 100 may cease to collect new ultrasound images, and ultrasound images displayed on the scan screen on the mobile device 104 may be frozen. In other words, the current ultrasound image on the scan screen may not be updated. In some embodiments, the two functions of a single press of the center button 219 described above (capturing an ultrasound image and capturing a cine) may only be performed when the ultrasound system 100 is not in low-power mode. In such embodiments, when the mobile device 104 receives an indication from the ultrasound probe 102 of a single press of the center button 219 and the ultrasound system 100 is in low-power mode, the mobile device 104 may cause the ultrasound system 100 to exit low-power mode, and the ultrasound system 100 may resume collection of ultrasound images, and ultrasound images will resume updating on the scan screen. In some embodiments, a user may configure the ultrasound system 100 (e.g., through a configuration screen displayed on the mobile device 104) as to whether a single press of the center button 219 should switch its function when the ultrasound system enters low-power mode. Further description of switching the function of the center button 219 may be found in [insert reference to our patent application on this feature].

In some embodiments, the mobile device 104 may perform an action when it receives an indication from the ultrasound probe 102 of a long press of the center button 219. In some embodiments, the action may be to capture a cine of ultrasound images. In particular, the mobile device 104 may begin to capture ultrasound images as a cine after detecting that the center button 219 has been pressed for a threshold period of time, and stop capturing the cine when the long press ends. In some embodiments, the action may be to disable all the buttons 218-220. This disabling may be temporary. In some embodiments, the action may be to display the button function configuration menu. For example, instead of or in addition to displaying the button function configuration menu (at step 304) based on receiving an indication of a double press of the center button 219 (at step 302), the mobile device 104 may display the button function configuration menu based on receiving an indication of a long press of the center button 219. In some embodiments, the action may be to toggle on or off one or more artificial intelligence (AI) features presented in conjunction with an ultrasound scan. For example, such AI features may include quality indicators indicating a quality of the ultrasound image currently displayed on the scan screen and/or anatomical labels indicating anatomical features present in the ultrasound image currently displayed on the scan screen.

Figure 6:
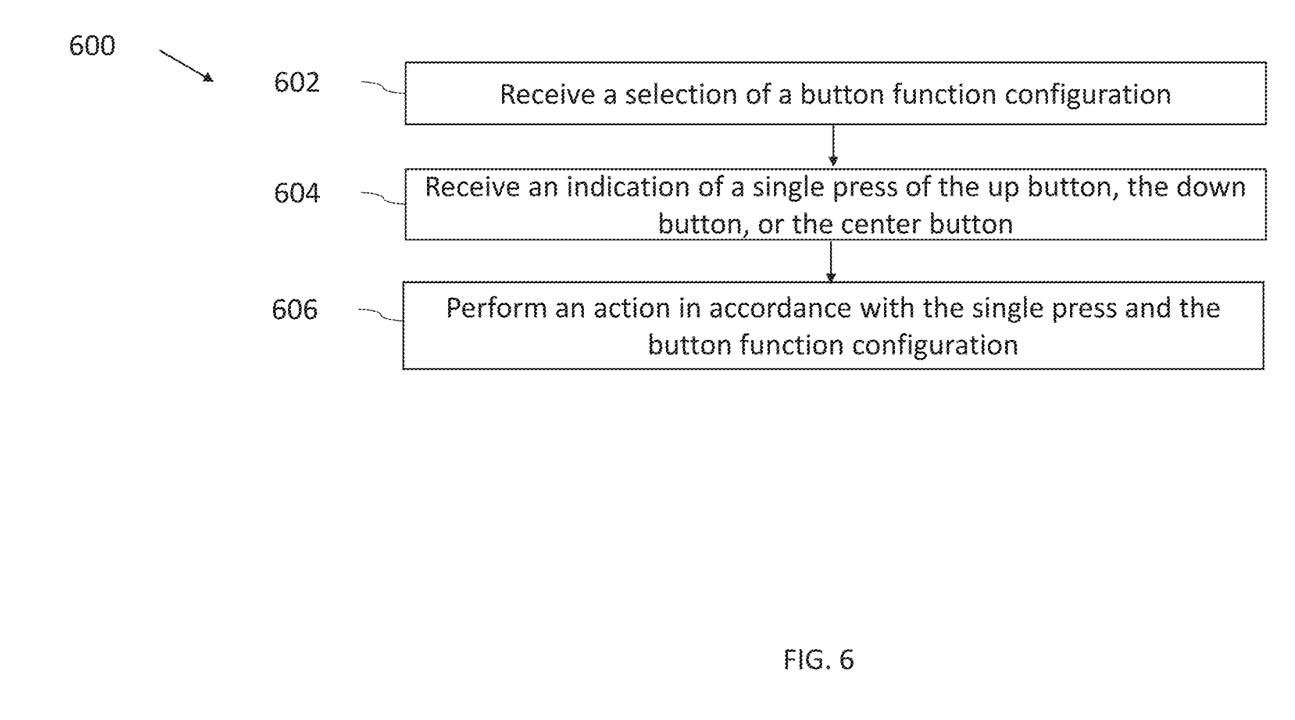
FIG. 6 illustrates an example of a process for configuration of the three buttons on the ultrasound probe, in accordance with certain embodiments described herein.

As described above, the process 300 may enable selection of functions for the up button 218 and the down button 220 during scanning, from the scan screen. Additionally or alternatively, the mobile device 104 may allow for selection of functions for the buttons 218-220 from a preferences screen, not during scanning. FIG. 6 illustrates an exemplary process 600 for configuration of the three buttons 218-220 on the ultrasound probe 102, in accordance with certain embodiments described herein. The process 600 may be performed by the mobile device 104.

At step 602, the mobile device 104 receives a selection of a button function configuration. For example, the mobile device 104 may display a button function configuration menu and receive a selection from the user of one of the options in the button function configuration menu. The button configuration menu may be displayed on a preferences screen, instead of a scan screen, where the preferences screen does not display any ultrasound images in real-time. Indeed, the ultrasound probe may not be collecting any ultrasound data when the mobile device 104 displays the preferences screen. Some of the button function configuration options available for selection may include, for example, any of the following:

1. Pressing the center button causes capture of an ultrasound image, pressing the up button causes increase in imaging depth, and pressing the down button causes decrease in imaging depth.
2. Pressing the center button causes capture of a cine of ultrasound images to start or stop, pressing the up button causes increase in imaging depth, and pressing the down button causes decrease in imaging depth.
3. Pressing the center button causes capture of an ultrasound image, pressing the up button causes increase in imaging gain, and pressing the down button causes decrease in imaging gain.
4. Pressing the center button causes capture of a cine of ultrasound images to start or stop, pressing the up button causes increase in imaging gain, and pressing the down button causes decrease in imaging gain.
5. Pressing the center button causes capture of an ultrasound image and pressing the up and down buttons causes change of mode.
6. Pressing the center button causes capture of a cine of ultrasound images to start or stop and pressing the up and down buttons causes change of mode.

Figure 7:
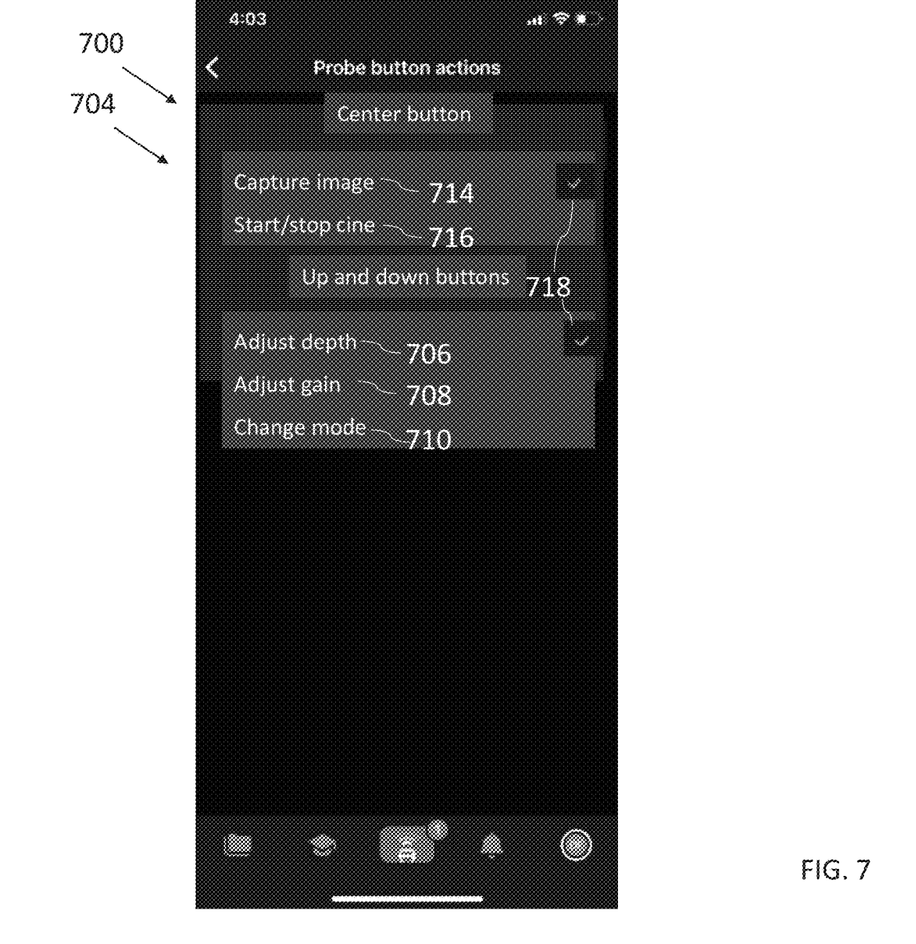
FIG. 7 illustrates an example of a preferences screen, in accordance with certain embodiments described herein.

FIG. 7 illustrates an exemplary preferences screen 700, in accordance with certain embodiments described herein. The preferences screen 700 displays a button function configuration menu 704 including multiple function options for the buttons 218-220. In particular, the button configuration menu 704 includes a capture image option 714 and a start/stop cine option 716 for the center button 219, and an adjust depth option 706, an adjust gain option 708, and a change mode option 710 for the up button 218 and the down button 220. In some embodiments, the user may select one of these options by touching the option, and a checkmark 718 may appear next to the selected option.

At step 604, the mobile device 104 receives an indication of a single press of the up button, the down button, or the center button. Further description of receiving indications of button presses may be found above with reference to the process 300.

At step 606, the mobile device 104 performs an action in accordance with the single press of the button (from step 604) and the selected button function configuration (from step 602). Further description of performing actions based on button presses may be found above with reference to the process 300.

Once a function or functions have been selected for some or all of the buttons 218-220 (e.g., using the process 600 or the process 300), the selected function may persist until the next time the user selects a new button function configuration menu. For example, in embodiments in which the button function configuration is selected from a button function configuration menu on the scan screen by (e.g., as described in the process 300), the selected configuration may persist until the user makes a new selection of a button function configuration from the button function configuration menu on the scan screen. As another example, in embodiments in which the button function configuration is selected from a preferences screen (e.g., as described in the process 600), the selected configuration may persist until the user makes a new selection of a button function configuration from the preferences screen. In some embodiments, if the user is logged into their account on the ultrasound application 106, the selected function for the buttons 218-220 may cease to persist after the user has logged out of their account. In particular, the mobile device 104 may save the selected button function configuration locally to the mobile device 104, and this saved configuration may not persist after a logout event. Thus, if the user logs into the ultrasound application 106 on a different mobile device 104, the button function configuration selected previously on the other mobile device 104 will not necessarily already be applied. In other words, the button function configuration may not be synchronized across devices. Alternatively or additionally, the selected function for the buttons 218-220 may cease to persist after the user has closed the ultrasound application 106. Alternatively or additionally, the selected function for the buttons 218-220 may cease to persist after the user has disconnected the ultrasound probe 102 from its wired or wireless connection to the mobile device 104. In other embodiments, the selection of the button function configuration may be uploaded to the cloud, associated with the particular user account being used currently, and retrieved from the cloud later by whichever mobile device 104 the user account is active on. In other words, the button function configuration may be synchronized across devices, and when a user logs into any mobile device 104 with a particular user account, the button function configuration associated with that account may be downloaded from the cloud for use by the mobile device 104.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

The invention claimed is:

1. An ultrasound system, comprising:
an ultrasound probe comprising:
  a transducer head;
  an external housing; and
  three buttons disposed on the external housing vertically along a direction of a longitudinal axis of the ultrasound probe, the three buttons comprising:
    an up button closest to the transducer head;
    a down button farthest from the transducer head; and
    a center button between the up button and the down button; and
a mobile device in operative communication with the ultrasound probe and running an ultrasound application, wherein the mobile device is configured to:
  receive an indication from the ultrasound probe of a double press of the center button when the mobile device is displaying a scan screen, wherein ultrasound data captured by the ultrasound probe and transmitted to the mobile device is displayed on the scan screen as ultrasound images that are updated in real-time;
  based on the receiving the indication of the double press of the center button, display a button function configuration menu on the scan screen;
  receive a selection from the button function configuration menu of a button function configuration;
  receive an indication of a single press of the up button or the down button; and
  perform an action in accordance with the single press of the up button or the down button and the button function configuration.

2. The ultrasound system of claim 1, wherein the button function configuration menu comprises multiple selectable options for functions of the up button and the down button, and the multiple selectable options comprise:
adjust depth;
adjust gain; and
change mode.

3. The ultrasound system of claim 1, wherein the button function configuration menu comprises:
a list of options; and
a selection indicator that highlights an option in the list; and the mobile device is configured, when receiving the selection from the button function configuration menu of the button function configuration, to:
  receive an indication from the ultrasound probe of a press of the up button or the down button and move a location of the selection indicator in the list up or down, respectively; and
  receive an indication from the ultrasound probe of a press of the center button and set the option in the list highlighted by the selection indicator as the button function configuration.

4. The ultrasound system of claim 1, wherein the button function configuration menu comprises a list of options, and the mobile device is configured, when receiving the selection from the button function configuration menu of the button function configuration, to detect a touch from a user of one of the options on a touch-sensitive display screen of the mobile device.

5. The ultrasound system of claim 1, wherein the mobile device is configured to overlay the button function configuration menu on the scan screen.

6. The ultrasound system of claim 1, wherein the selected button function configuration is adjusting imaging depth, and the mobile device is configured, when performing the action, to receive an indication from the ultrasound probe of a press of the up button or the down button and cause the imaging depth to increase or decrease, respectively.

7. The ultrasound system of claim 6, wherein the mobile device is configured to cause the imaging depth to increase or decrease by 1 cm for a single button press.

8. The ultrasound system of claim 6, wherein the mobile device is configured, when causing the imaging depth to increase or decrease, to transmit one or more commands to the ultrasound probe to change one or more aspects of how the ultrasound probe transmits ultrasound waves.

9. The ultrasound system of claim 8, wherein the one or more aspects are selected from the group consisting of pulse repetition rate, focal depth, frequency, pulse length, and aperture size.

10. The ultrasound system of claim 1, wherein the selected button function configuration is adjusting gain, and the mobile device is configured, when performing the action, to receive an indication from the ultrasound probe of a press of the up button or the down button and cause the imaging gain to increase or decrease, respectively.

11. The ultrasound system of claim 10, wherein the mobile device is configured to cause the imaging gain to increase or decrease by 5% for a single button press.

12. The ultrasound system of claim 1, wherein the selected button function configuration is adjusting mode, and the mobile device is configured, when performing the action, to receive an indication from the ultrasound probe of a press of the up button or the down button and to cycle through a list of ultrasound imaging modes including two or more of B-mode, color Doppler, power Doppler, M-mode, and pulsed Doppler.

13. The ultrasound system of claim 12, wherein the mobile device is configured, when cycling through the list of ultrasound imaging modes, to transmit one or more commands to the ultrasound probe to change one or more aspects of how the ultrasound probe transmits ultrasound waves and/or one or more aspects of how the ultrasound probe receives ultrasound waves.

14. The ultrasound system of claim 1, wherein a user is logged into an account on the ultrasound application, and the button function configuration persists until the user logs out of the account on the ultrasound application.

15. The ultrasound system of claim 1, wherein the mobile device is configured to save the button function configuration locally.

16. The ultrasound system of claim 1, wherein the selected button function configuration is adjusting imaging depth, and the mobile device is configured, when performing the action, to receive an indication from the ultrasound probe of a long press of the up button or the down button and cause the imaging depth to continuously increase or decrease, respectively.

17. The ultrasound system of claim 1, wherein the selected button function configuration is adjusting gain, and the mobile device is configured, when performing the action, to receive an indication from the ultrasound probe of a long press of the up button or the down button and cause the imaging gain to continuously increase or decrease, respectively.

18. The ultrasound system of claim 1, wherein the mobile device is configured to receive an indication from the ultrasound probe of a long press of the center button and perform an action selected from the group consisting of:
  capturing a cine of ultrasound images;
  disabling the up button, the down button, and the center button;
  display the button function configuration menu; and
  toggle on or off one or more artificial intelligence features.

19. An ultrasound system, comprising:
  an ultrasound probe comprising:
    a transducer head;
    an external housing; and
    three buttons disposed on the external housing vertically along a direction of a longitudinal axis of the ultrasound probe, the three buttons comprising:
      an up button closest to the transducer head;
      a down button farthest from the transducer head; and
      a center button between the up button and the down button; and
  a mobile device in operative communication with the ultrasound probe and running an ultrasound application, wherein the mobile device is configured to:
    receive a selection from a preferences screen of a button function configuration from among a plurality of button function configuration options comprising:
      pressing the center button causes capture of an ultrasound image, pressing the up button causes increase in imaging depth, and pressing the down button causes decrease in imaging depth;
      pressing the center button causes capture of a cine of ultrasound images to start or stop, pressing the up button causes increase in imaging depth, and pressing the down button causes decrease in imaging depth;
      pressing the center button causes capture of an ultrasound image, pressing the up button causes increase in imaging gain, and pressing the down button causes decrease in imaging gain; and
      pressing the center button causes capture of a cine of ultrasound images to start or stop, pressing the up button causes increase in imaging gain, and pressing the down button causes decrease in imaging gain;
    receive an indication of a single press of the up button, the down button, or the center button; and
    perform an action in accordance with the single press of the up button, the down button, or the center button, and the selected button function configuration.

20. The ultrasound system of claim 19, wherein the plurality of button function configuration options further comprise:
  pressing the center button causes capture of an ultrasound image and pressing the up and down buttons causes change of mode; and
  pressing the center button causes capture of a cine of ultrasound images to start or stop and pressing the up and down buttons causes change of mode.

* * * * *